(12) United States Patent
Beyens

(10) Patent No.: US 10,488,304 B2
(45) Date of Patent: Nov. 26, 2019

(54) DIRECT ANALYSIS SAMPLER WITH HEAT SINK

(71) Applicant: HERAEUS ELECTRO-NITE INTERNATIONAL N.V., Houthalen (BE)

(72) Inventor: Dries Beyens, Kinrooi (BE)

(73) Assignee: HERAEUS ELECTRO-NITE INTERNATIONAL N.V., Houthalen (BE)

( * ) Notice: Subject to any disclaimer, the term of this patent is extended or adjusted under 35 U.S.C. 154(b) by 153 days.

(21) Appl. No.: 15/837,190

(22) Filed: Dec. 11, 2017

(65) Prior Publication Data

US 2018/0164191 A1  Jun. 14, 2018

(51) Int. Cl.
*G01N 21/03* (2006.01)
*G01N 1/12* (2006.01)
*G01N 21/01* (2006.01)
*G01N 21/69* (2006.01)
(Continued)

(52) U.S. Cl.
CPC ............ *G01N 1/125* (2013.01); *G01N 21/01* (2013.01); *G01N 21/69* (2013.01); *G01N 33/205* (2019.01); *G01N 21/03* (2013.01); *G01N 2001/1068* (2013.01); *G01N 2021/0193* (2013.01); *G01N 2021/695* (2013.01)

(58) Field of Classification Search
CPC ...... G01N 1/125; G01N 33/205; G01N 21/03; G01N 21/69
See application file for complete search history.

(56) References Cited

U.S. PATENT DOCUMENTS

| 3,646,816 A | 3/1972 | Hance et al. |
| 4,211,117 A | 7/1980 | Cure |
| 4,401,389 A | 8/1983 | Theuwis |

(Continued)

FOREIGN PATENT DOCUMENTS

| EP | 0128665 A2 | 12/1984 |
| JP | 2004012339 A | 1/2004 |

(Continued)

OTHER PUBLICATIONS

Dulski, T.R., "A manual for the chemical analysis of metals," Mar. 31, 1996, ASTM International, USA, XP055372569, vol. MNL25, pp. 1-16.

(Continued)

*Primary Examiner* — Jamel E Williams
(74) *Attorney, Agent, or Firm* — Blank Rome LLP

(57) ABSTRACT

A sample chamber assembly for molten metal comprises a cover plate and a housing. A first face of the housing has a depression in direct flow communication with a first opening formed at the immersion end of the housing. The cover plate and the housing are assembled together along a first plane to form a sample cavity including the depression. An analysis surface of a solidified metal sample lies in the first plane. The sample cavity and the first opening are aligned along a common longitudinal axis. The first opening is spaced apart from the first plane. A ratio of the thermal diffusivities of the solidified metal sample and the housing material is between 0.1 and 0.5. The housing is inseparable from the solidified metal sample. A portion of the housing is directly adjacent to the solidified metal sample and lies in the first plane.

17 Claims, 12 Drawing Sheets

(51) Int. Cl.
*G01N 33/205* (2019.01)
*G01N 1/10* (2006.01)

(56) References Cited

U.S. PATENT DOCUMENTS

| | | | |
|---|---|---|---|
| 5,415,052 | A | 5/1995 | Baerts |
| 9,128,013 | B2 | 9/2015 | Song et al. |
| 9,645,055 | B2 | 5/2017 | Cappa et al. |
| 2012/0293798 | A1 | 11/2012 | Song et al. |
| 2014/0053647 | A1* | 2/2014 | Beyens ............ G01N 1/125 |
| | | | 73/431 |
| 2014/0119404 | A1* | 5/2014 | Beyens ............ G01N 27/411 |
| | | | 374/140 |
| 2014/0318276 | A1 | 10/2014 | Cappa et al. |
| 2017/0248499 | A1* | 8/2017 | Pitts-Baggett ...... G01N 1/125 |
| 2018/0164191 | A1* | 6/2018 | Beyens ............ G01N 21/69 |
| 2018/0164192 | A1* | 6/2018 | Beyens ............ G01N 33/205 |
| 2018/0164193 | A1* | 6/2018 | Beyens ............ G01N 33/205 |
| 2018/0164195 | A1* | 6/2018 | Beyens ............ G01N 1/12 |

FOREIGN PATENT DOCUMENTS

| | | |
|---|---|---|
| JP | 2012242396 A | 12/2012 |
| KR | 20120129781 A | 11/2012 |
| SU | 709973 A1 | 1/1980 |
| SU | 1161840 A1 | 6/1985 |
| UA | 48949 U | 4/2010 |
| WO | WO-9624829 A1 | 8/1996 |

OTHER PUBLICATIONS

European Search Report issued in EP Application No. 16203811.1 dated Jun. 16, 2017.

\* cited by examiner

DIRECT ANALYSIS SAMPLER WITH HEAT SINK

CROSS REFERENCE TO RELATED APPLICATION

This application claims the benefit of EP Application No. 16203811.1, filed Dec. 13, 2016, the contents of which are incorporated by reference herein in its entirety.

TECHNICAL FIELD

The invention relates to a low volume, low mass, solidified sample of molten metal, particularly molten steel or molten iron, which can be directly analyzed on an optical emission spectrometer. The invention also relates to the physical arrangement of a molten metal immersion sampling device for retrieving a molten sample which is capable of quick chilling to produce a crack free coupon of metal that can be immediately analyzed on an optical emission spectrometer without surface preparation. The invention further relates to a low volume, low mass, metal sample which is unheated by the analysis process itself, thereby leading to higher accuracy of the analysis results.

BACKGROUND

During the processing of metals in their molten state, it is necessary to obtain a representative sample of the molten metal at various stages of the process, for example, for the analysis or evaluation of either the chemical composition or the metallographic structure of the metal sample. Different methods for analyzing molten metals during manufacturing and further processing are known in the art.

Historically, the composition of a solidified metal sample is often determined using arc spark-optical emission spectroscopy ("OES") equipment. OES systems are generally the most effective systems for determining the chemical composition of a metal sample and for controlling the processing of molten metals due to their rapid analysis times and inherent accuracy. Thus, OES analysis is typically used during molten metal processes for controlling the progress of molten metal production.

OES involves exciting atoms of a target sample of which knowledge of the composition is desired, and examining the wavelength of photons emitted by atoms during transition from an excited state to a lower energy state. Each element in the periodic table emits a characteristic set of discrete wavelengths when its atoms return from an excited state to a lower energy state. By detecting and analyzing these wavelengths, the elemental composition of a sample can be determined in accordance with a calibration curve, thereby showing the relationship between the spectral intensity ratio (i.e., absolute radiation power of an element/absolute radiation power of the base metal) and the concentration of the element in the standard sample.

The spectral light may be produced by irradiation with electromagnetic radiation, such as by a laser or x-rays, but is generally produced for OES by a short spark produced by a spark generator incident upon the target of which knowledge of its elemental composition is desired. In this case, the target is the metal sample. Spark generators, their intensity and their pulse regime vary according to the specific OES equipment. Irrespective of the spark energy input, the accuracy and reliability of such emission spectrometers has been known to be dependent on the accuracy and quality of the detector and optics used to receive the radiation emitted from the sample and the homogeneity of the metal sample itself.

Broadly speaking, the OES analysis procedure begins with the conductive metal sample being positioned with its analysis surface face down on a predetermined region of the stage of the OES instrument, namely an optical emission spectrometer. More particularly, the sample is positioned so as to span and close the analysis opening of the spectrometer and an anode nearly abuts the analysis surface of the sample. Once the desired positioning of the sample and proximity of the anode and analysis surface is achieved, a spark is discharged between the anode and the conductive metal sample which is electrically connected to the spectrometer stage. This connection is, in most cases, made by gravitational force in combination with a small load. The analysis opening on the optical emission spectrometer is typically around 12 mm wide. This distance avoids that a spark arcs between the anode and the instrument housing. The optical detector receives the emitted light from the excavated material of the sample surface. The spark chamber, formed in part by the space between the anode and the metal sample, is continuously purged with argon or other inert gas in order to avoid air ingress which would lead to erroneous analysis values.

In order to lay flat upon the analysis opening of the spectrometer, the metal sample cannot have any extensions and the analysis surface of the metal sample must be smooth. There can be no part of the sample or sample housing which will break the plane of the analysis surface. The sample must span the analysis opening of the spectrometer and be of sufficient flatness to facilitate inert gas purging of the spark chamber and present a contiguous sample surface toward the anode.

The procedures and processes to obtain a representative analysis of metals are well known in the art as described in In Dulski, T. R. *A Manual for the Chemical Analysis of Metals*, ASTM International, 1996. Until know, it has been generally believed that the metal sample and the instrumentation used for its analysis are independent of each other and, as such, one does not influence the other.

Conventional sampling devices which provide a coupon or disc of solid metal for use in spectrographic analysis are known. The geometric shape and dimensions of the solidified metal coupons obtained by such sampling devices will sometimes be specific to the type of metal or metallographic need. A general category of samples that are obtained by immersion devices for OES analysis are samples having a disc or oval shape and a diameter or long length of 28-40 mm. Most commonly, such samples have a diameter or long length of about 32 mm and a thickness of 4-12 mm. Some samplers, commonly known as lollipop samplers, may produce a differently shape sample, ranging from round to oval or longer, according to the requirements of the user, but most samples still have a diameter or long length of about 32 mm. Other samplers, commonly known as dual thickness samplers, combine two thicknesses within the same sample.

Typical sampling devices designed to obtain samples of molten metal for analysis by OES include a sample chamber or mold cavity configured to be filled with molten metal upon immersion of the sampling device into the molten metal bath. The molds which delineate the mold cavity or sampling chamber are typically either a two-part clam shell type arrangement or a ring covered on its upper and lower sides by flat plates. Once the sample of metal is solidified, the molds are discarded and the sample is transported to the OES for analysis.

U.S. Pat. No. 3,646,816 describes this type of expendable immersion sampler, in which both flat surfaces of a disc-like sample are formed by chill-plates to achieve more rapid freezing and a pair of smoother surfaces which require less clean-up prior to analysis. Other prior art patents, such as U.S. Pat. No. 4,211,117, relate to a similar concept, while U.S. Pat. Nos. 4,401,389 and 5,415,052 provide examples of this metallurgical sample being combined with other sensors, one of which could be a temperature measuring sensor.

Samples produced by conventional sampling devices have a diameter of about 32 mm in a direction parallel to the spectrometer opening and a thickness of 4-12 mm in a direction perpendicular to the spectrometer opening. It has been found that a solidified sample of conventional thicknesses requires surface grinding from 0.8 to 5 mm of the as-cast surface, in order to achieve an analysis surface which is free from metal and non-metallic segregation. Conventional samples can only achieve this surface state after preparation processes to produce a geometry that is typically at least 28 mm in diameter in a direction parallel to the spectrometer opening and has a thickness which is typically less than 12 mm in a direction perpendicular to the opening. This after-preparation geometry can be easily handled by pre-analysis preparation equipment that mechanically grinds the sample surface and is also convenient for handling by robotic manipulators which advance the sample from preparation through analysis and removal to await the next sample.

Eliminating the need for surface preparation speeds the analysis time and is economically favorable to the metal producer. However, this could only be achieved by a uniform filling of the sample cavity and rapid chilling of the molten metal sample, such that the entire sample section presented for analysis freezes uniformly and without surface oxidation. The heat content of the solidifying metal must be removed to bring the sampled metal to near room temperature before it is removed from the sampling chamber molds. Exposing the hot metal surface to air will quickly form oxides on its surface which must be later removed by mechanical grinding in order to be analyzed by optical emission spectroscopy.

Unnecessary constraints imposed upon the shape and size of the metal sample for OES, discussed later, result in the prior art sample volume being over dimensioned from the minimum volume of metal required to arrive at the minimum necessary analyzed surface. The unnecessary large sample volumes of the prior art devices thus preclude rapid solidification of the molten metal sample. As such, conventional devices cannot be reliably analyzed by OES without surface preparation and thereby potential economic benefit is lost.

Direct Analysis (DA) samplers are a newly developed type of molten metal immersion sampler which produce DA samples. DA samples do not require any kind of surface preparation before being analyzed, and thus can result in significant economic benefit both in terms of the availability of timely chemistry results as well as laboratory time savings by utilizing the OES analysis method.

U.S. Pat. No. 9,128,013 discloses a sampling device for retrieving a rapid chilled sample from a converter process for making steel that is intended for local analysis. The sampling device includes a sample chamber formed by at least two parts, where the specified ratio of the mass of the melt taken up in the sample cavity to the mass of the sample chamber assembly enables a rapid cooling of the melt filling the sample cavity. When this sample chamber is removed from the measuring probe, thereby exposing the sample surface to atmosphere, the melt has already cooled sufficiently that oxidation is prevented to the greatest extent possible, and therefore post-treatment of the sample surface is unnecessary. In addition, the fast solidification and thin sample offers a solution to the problem of elemental segregation of the prior art 12 mm thick samples, again promoting the elimination of surface grinding before analysis.

A similar DA type sampler is known from U.S. Patent Application Publication No. 2014/318276. One end of the sample cavity of this DA type sampler is connected to the molten metal bath during immersion of the sampler via an inflow conduit, while an opposite end of the sample cavity is in communication with a coupling device. During immersion, but before the filling of the sample cavity with the molten metal, the sample cavity is purged with an inert gas to avoid early filling and oxidation of the sampled material. This device, as well as the prior described sampling device, has a geometry in which the inflow conduit is arranged perpendicular to the flat surface of the sample cavity and thus perpendicular to the analysis surface. While the analysis surface is free and readily presentable to the OES spark source, it has been found that the sample is inhomogeneous.

SUMMARY OF THE INVENTION

The invention relates to a rapid chilled sampler which is filled with molten metal in the immersion direction parallel to the longitudinal axis and which produces a metallurgical sample analyzed on an OES without surface preparation. Part of the mold which is responsible for the largest chill mass is inseparable from the sample itself. Accordingly, the sample housing, rather than the sample itself, is configured to provide the greatest utility on existing optical emission spectrographs which, at present, require an analyzable surface to be of certain dimensions.

In summary, the following embodiments are proposed as particularly preferred in the scope of the invention:

Embodiment 1

A sample chamber assembly for molten metal, the sample chamber assembly comprising:
a cover plate and a housing,
characterized in that the housing includes:
an immersion end having a first opening for a molten metal inflow conduit and an opposing end; and
a first face extending between the immersion end and the opposing end, the first face having a depression extending from proximate the immersion end toward the opposing end, the depression being in direct flow communication with the first opening and configured to receive the molten metal from the inflow conduit,
wherein the cover plate and the housing are configured to be assembled together along a first plane to form a sample cavity including the depression, such that an analysis surface of a solidified metal sample formed within the sample cavity lies in the first plane,
wherein the sample cavity and the first opening are aligned along a common longitudinal axis,
wherein the first opening is spaced apart from the first plane,
wherein a ratio of the thermal diffusivity of the solidified metal sample to the thermal diffusivity of a material forming the housing is between 0.1 and 0.5, preferably 0.2, and wherein the housing is configured to be inseparable from the solidified metal sample and at least a portion of the housing is directly adjacent to the solidified metal sample and lies in the first plane.

Embodiment 2

A sample chamber assembly according to the preceding embodiment, characterized in that a ratio of a mass of the sample chamber to a mass of the molten metal received within the sample collection volume is 9 to 12, preferably 10.

Embodiment 3

A sample chamber assembly according to any of the preceding embodiments, characterized in that a depth of the depression is 0.5 mm to 3 mm.

Embodiment 4

A sample chamber assembly according to any of the preceding embodiments, characterized in that the housing further includes a ridge protruding from the first face and surrounding the depression, a combined width of the depression and adjacent portions of the ridge being in the range of 10 mm to 30 mm.

Embodiment 5

A sample chamber assembly according to any of the preceding embodiments, characterized in that there are no increases in a width dimension of the sample cavity in a flow direction of the molten metal from the end of the distribution zone toward the opposing end.

Embodiment 6

A sample chamber assembly according to any of the preceding embodiments, characterized in that a ratio of the length to depth of the sample cavity increases in a flow direction of the molten metal from the inflow conduit toward the opposing end.

Embodiment 7

A sample chamber assembly according to any of the preceding embodiments, characterized in that a total length of the depression is between 25 and 35 mm, preferably 30 mm.

Embodiment 8

A sample chamber assembly according to any of the preceding embodiments, characterized in that the depression has a uniform depth and a cross-sectional area of the depression gradually tapers in the flow direction of the molten metal from the inflow conduit toward the opposing end.

Embodiment 9

A sample chamber assembly according to any of the preceding embodiments, characterized in that the solidified metal sample is formed as an elongated strip or rectangle.

Embodiment 10

A sample chamber assembly according to any of the preceding embodiments, characterized in that the cover plate includes a sealing member configured to provide a substantially gas-tight seal between the cover plate and the housing.

Embodiment 11

A sample chamber assembly according to any of the preceding embodiments, characterized in that the cover plate is secured to the housing by a metal clamp to form the sample chamber.

Embodiment 12

A sample chamber assembly according to any of the preceding embodiments, characterized in that a cross-sectional area of the inflow conduit is between 0.5 and 2 times of a cross-sectional area of the depression.

Embodiment 13

A sample chamber assembly according to any of the preceding embodiments, characterized in that when the cover plate and the housing are assembled together, the cover plate sits flush against the ridge of the housing along the first plane.

Embodiment 14

The use of a sampler having the sample chamber assembly according to any of the preceding claims for obtaining a solidified metal sample that is inseparably contained with the housing of the sample chamber assembly.

BRIEF DESCRIPTION OF DRAWINGS

The foregoing summary, as well as the following detailed description of preferred embodiments of the invention, will be better understood when read in conjunction with the appended drawings. For the purpose of illustration, there are shown in the drawings embodiments which are preferred. It should be understood, however, that the device and method are not limited to the precise arrangements and instrumentalities shown.

DETAILED DESCRIPTION

The invention relates to an immersion sampling probe for producing a solidified strip metal sample for direct analysis by OES.

Figure 1:
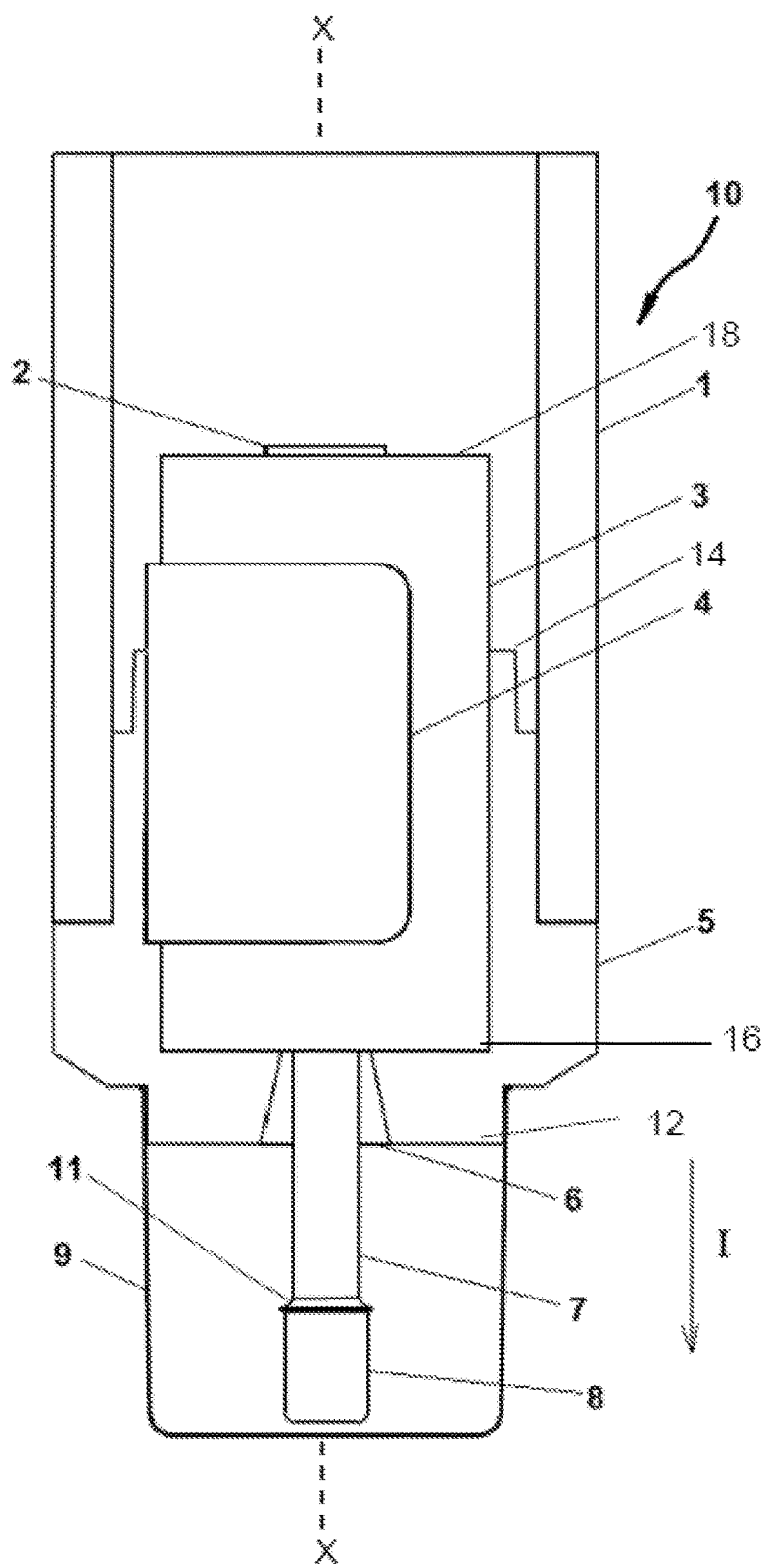
FIG. 1 is a side elevational view of an immersion sampling probe oriented in the immersion direction in accordance with one embodiment of the invention.

Referring to FIG. 1, there is shown an immersion sampling probe 10, and more particularly a molten metal sampling probe 10. Most preferably, the probe 10 is suitable for immersion in and sampling of molten steel or iron. The probe 10 comprises a measuring head 5. The measuring head 5 is preferably made of resin bonded silica sand. However, it will be understood by those skilled in the art that the measuring head 5 may be made of any material known to be suitable for forming a body to be immersed in molten metal.

The measuring head 5 is supported on a carrier tube 1. Preferably, the carrier tube 1 is a paper carrier tube. In use, a probe holder or lance (not shown) is preferably inserted into the interior volume of the carrier tube 1 to provide the mechanical action necessary to submerse the measuring head 5 below the surface of a bath of molten metal (not shown) in the immersion direction I.

The measuring head 5 comprises a sample chamber 3 for collection and retrieval of a sample of molten metal. It will be understood by those skilled in the art that while the sample chamber 3 is described herein in terms of the immersion sampling probe 10, the sample chamber 3 may be utilized with any type of molten metal sampling device. Thus, the assembly and configuration of the sample chamber 3 described herein is applicable to any type of molten metal sampling device, not just the immersion sampling probe 10.

Preferably, the sample chamber 3 is a two-part sampling chamber. More particularly, referring to FIG. 2, the sample chamber 3 is composed of a housing 30 and cover plate 32. The housing 30 is preferably formed of one or more materials which are good thermal and electrical conductors, such as, but not limited to, aluminum, copper and other metals having similar thermal and electrical conductivity properties for being electrically coupled to the retrieved metal sample. Preferably, the housing 30 is made of aluminum. The mass of the closing plate 32 preferably accounts for 10 to 20% of the overall mass of the sample chamber 3. The housing 30 may be marked by an indestructible method with identification means.

The two parts 30, 32 of the sample chamber 3 are preferably held together by a clamp 4 (also referred to as a clip) with a compression force sufficient to resist a tendency of the two parts 30, 32 of the sampling chamber 3 to separate due to the force of molten metal flowing into and filling the sample chamber 3. The clamp 4 is preferably a metal clamp. However, it will be understood by those skilled in the art that the clamp 4 may be made of another suitable material which is capable of immersion in molten metal and provides the requisite compressive force.

Referring to FIG. 1, the measuring head 5 has a first end 12 and an opposing second end 14. The first end 12 of the measuring head 5 corresponds to an immersion end. The second end 14 of the measuring head 5 is configured to face the lance or probe holder. The sample chamber 3 has a first end 16 and an opposing second end 18. The first end 16 of the sample chamber 3 corresponds to an immersion end. It will be understood by those skilled in the art that the phrase "immersion end" means the end of the body which is first immersed into molten metal in the immersion direction I.

The sample chamber 3 includes a sample cavity configured to receive molten metal, as described in greater detail herein. The sample cavity extends from proximate the first end 16 toward the second end 18 of the sample chamber 3 along a longitudinal axis X (see FIG. 4).

The first end 16 of the sample chamber 3 is preferably attached to or otherwise provided with an inflow conduit 7. More particularly, the first end 16 of the sample housing 30 has a first opening 20 for receiving the inflow conduit 7 (see FIG. 4). The first opening 20 and thus the inflow conduit 7 are preferably aligned with the sample chamber 3, and more particularly the sample cavity. The inflow conduit 7 enables the flow of molten metal from the molten metal bath into the sample chamber 3. Thus, molten metal is introduced into the sample cavity of the sample chamber 3 in the immersion direction parallel to the longitudinal axis X of the sample cavity. The inflow conduit 7 is preferably made of a quartz material, more preferably a fused quartz material. However, it will be understood that the inflow conduit 7 may be made of any other suitable material, including, but not limited to, a ceramic material.

Figure 4:
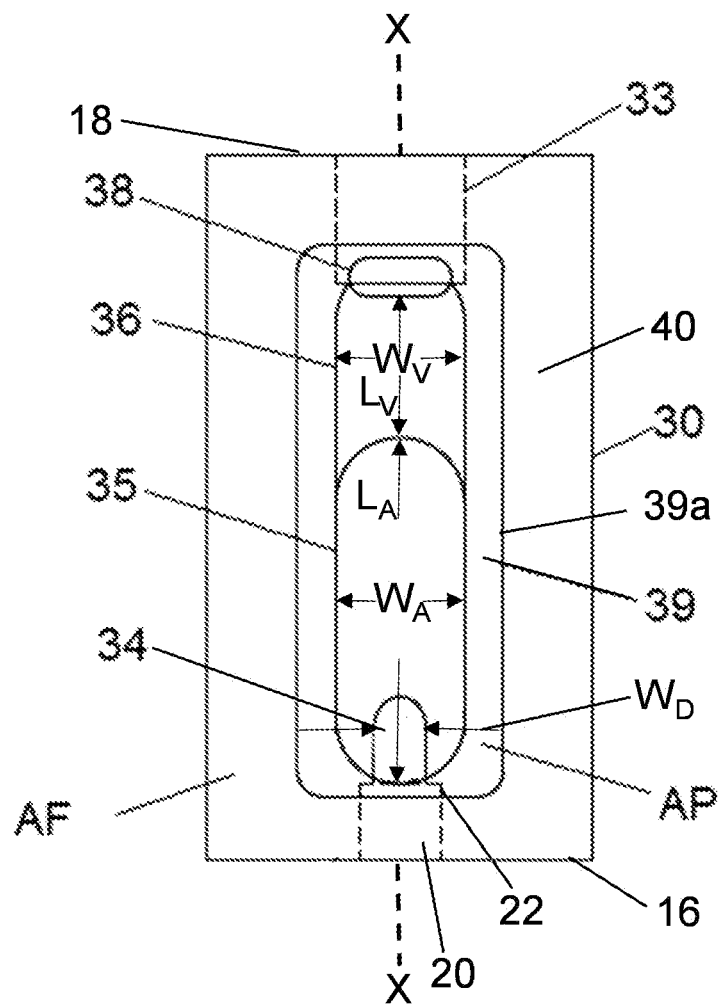
FIG. 4 is a front elevational view of the housing of a two-part sample chamber of the immersion sampling probe of FIG. 1.
Figure 4A:
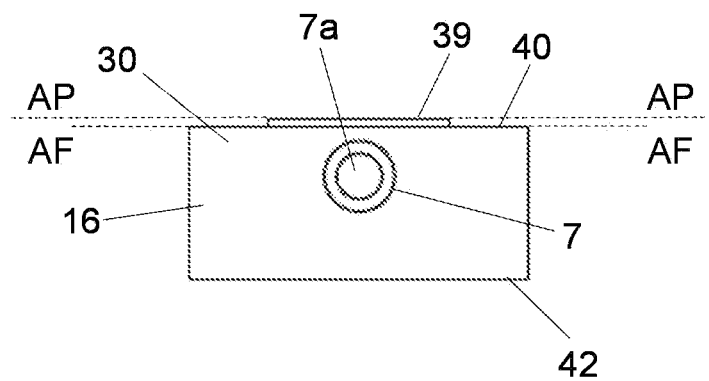
FIG. 4A is a bottom plan view of the sample chamber housing shown in FIG. 4.

The inflow conduit 7 has a first end (not shown) and an opposing second end 22 (see FIGS. 4-4A). In one embodiment, the inflow conduit 7 is secured within the measuring head 5 by a bushing 6 (see FIG. 1). The bushing 6 is preferably made of a cement material. The second end 22 of the inflow conduit 7 is adhered or attached within the sample chamber 3 by an adhesive 27 in a substantially gas tight manner. More particularly, the second end 22 of the inflow conduit 7 is positioned entirely within the first opening 20 of the housing 30 of the sample chamber 3 and is adhered therein by the adhesive 27 to achieve a substantially gas tight joint. "Substantially gas tight" means that the seal or joint may be completely gas tight or gas tight to a large degree. In particular, regarding the joining of the inflow conduit 7 and the gas coupler 2 (described herein), the joints formed are preferably gas tight to the extent that the sample cavity is capable of being pressurized above the pressure level at the immersion depth.

Figure 3:
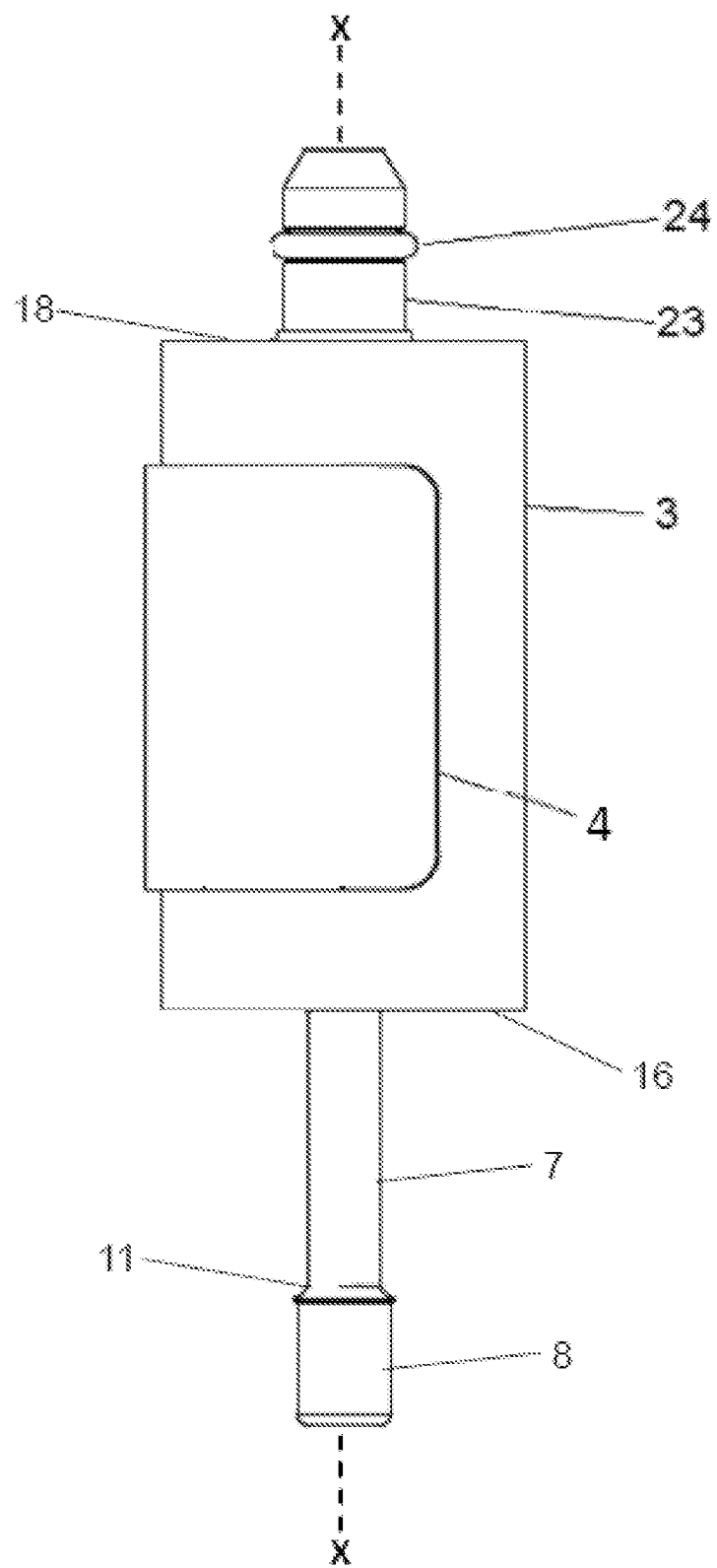
FIG. 3 is a side elevational view of the immersion sampling probe of FIG. 1 provided with a gas connector for connecting to a probe holder containing a pneumatic line.

Referring to FIGS. 1 and 3, the first end of the inflow conduit 7 corresponds to an immersion end. The first end is not visible on FIGS. 1 and 3, because it is covered by a first protection cap 8. More particularly, the first protection cap 8 is attached to the first end of the inflow conduit 7 in a substantially gas tight manner by adhesive 11. The first protection cap 8 is preferably made of metal, and more preferably steel. The first protection cap 8 may include an opening (not shown) (e.g., a 1 mm diameter hole) to ensure that the sample cavity can be sufficiently purged and that all entrapped air can be evacuated therefrom. A second protection cap 9, in turn, covers (and more specifically encompasses) the first protection cap 8. The second protection cap 9 is attached to the first end 12 of the measuring head 5. Preferably, the second protection cap 9 is made of metal, and more preferably steel. In one embodiment, the second protection cap 9 is further protected by a covering of paper (not shown).

Figure 2:
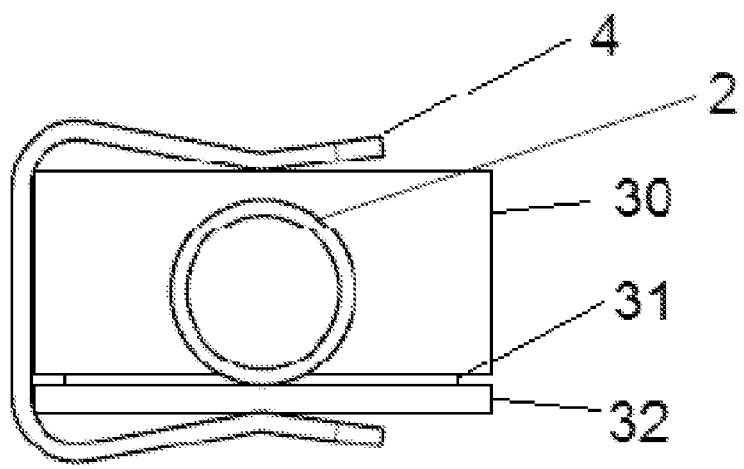
FIG. 2 is a top plan view of the immersion sampling probe of FIG. 1.

Referring to FIGS. 1-2 and 4, the second end 18 of the sample housing 30 includes a second opening 33 for receiving a coupler 2, and more particularly a gas coupler 2. The second opening 33 is thus a gas port which is preferably wholly contained within the housing 30. The coupler 2 is sealed to the housing 30 within the gas port 33 at the second end 18 of the sample chamber by an adhesive 26 to achieve a substantially gas tight joint. Thus, an end of the coupler 2 is positioned entirely within the body of the housing 30 of the sample chamber 3.

The coupler 2 is configured to mate with a conduit (not shown), and more particularly a gas conduit. More particularly, a first end of the gas conduit is attached to the coupler 2 and an opposing second end of the gas conduit is attached to a pneumatic system (not shown). The pneumatic system preferably supplies an inert gas to the sample chamber 3 via the gas conduit for purging and pressurizing the sample chamber 3. Examples of the inert gas which may be used to purge and pressurize the sample chamber 3 include, but are not limited to, nitrogen or argon. Preferably, the inert gas (e.g., nitrogen or argon) is at a pressure of 2 bar. The pneumatic system also facilities the removal of exhaust gases from the sample chamber 3 via the gas conduit. When a pneumatic system is in communication with the sampling chamber 3 of the probe 10 via the coupler 2, there is a continuous gas path from the immersion end of the inflow conduit 7 to the sampling chamber 3 (i.e., along the longitudinal axis X) that is substantially leak-free, yet the sample chamber 3 is easily disassembled in order to access the sample.

Referring to FIG. 3, in one embodiment, the coupler 2 is provided with a gas connector 23 configured to mate with a corresponding receptacle on the probe holder. More particularly, the gas connector 23 is a push-on/pull-off type of connector assembly and includes an O-ring 24 for gas sealing to a mating surface on the probe holder.

In use, the measuring head 5 is immersed into a molten metal bath and the sample chamber 3 is purged and pressurized by the inert gas which is supplied by the pneumatic system and which travels from the coupler 2 toward the inflow conduit 7 along the longitudinal axis X. After the measuring head 5 is immersed below the surface of the molten metal bath, the second protection cap 9 and the covering of paper (if present) melt due to the heat of the molten metal, thereby exposing the first protection cap 8 to the molten metal. Subsequently, the first protection cap 8 also melts, thereby placing the sample chamber 3 in fluid communication with the molten metal bath via the inflow conduit 7. More particularly, once the second protection cap 8 melts, the pressure of the inert gas exits from the sample chamber 3 via the open inflow conduit 7 (i.e., via the first end of the inflow conduit 7) until the pneumatic system reverses from a purge mode to an exhaust or vacuum mode. Molten metal then enters the sample chamber 3 through the inflow conduit 7, particularly from the first end to the second end 22 and subsequently into the sample cavity of the sample chamber 3, while gas is exhausted out of the sample chamber 3 through the coupler 2. The gas is preferably exhausted by the natural ferro-static pressure of the filling molten metal but may also be exhausted by a slight vacuum applied to the gas conduit by remote equipment.

Figure 5:
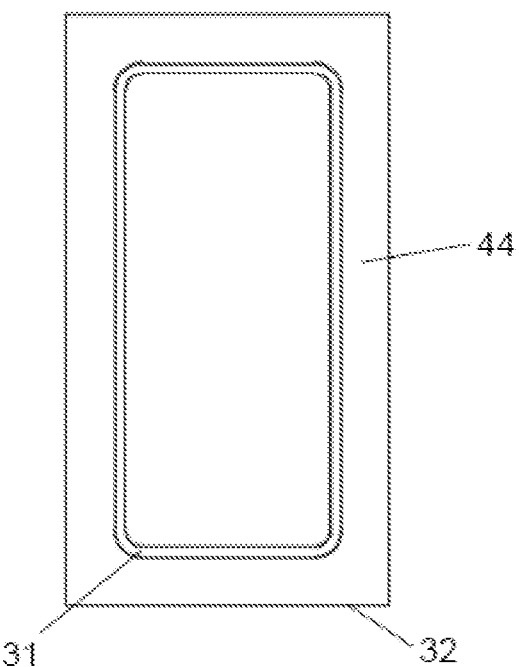
FIG. 5 is a front elevational view of the cover plate of the two-part sample chamber of the immersion sampling probe of FIG. 1.
Figure 6:
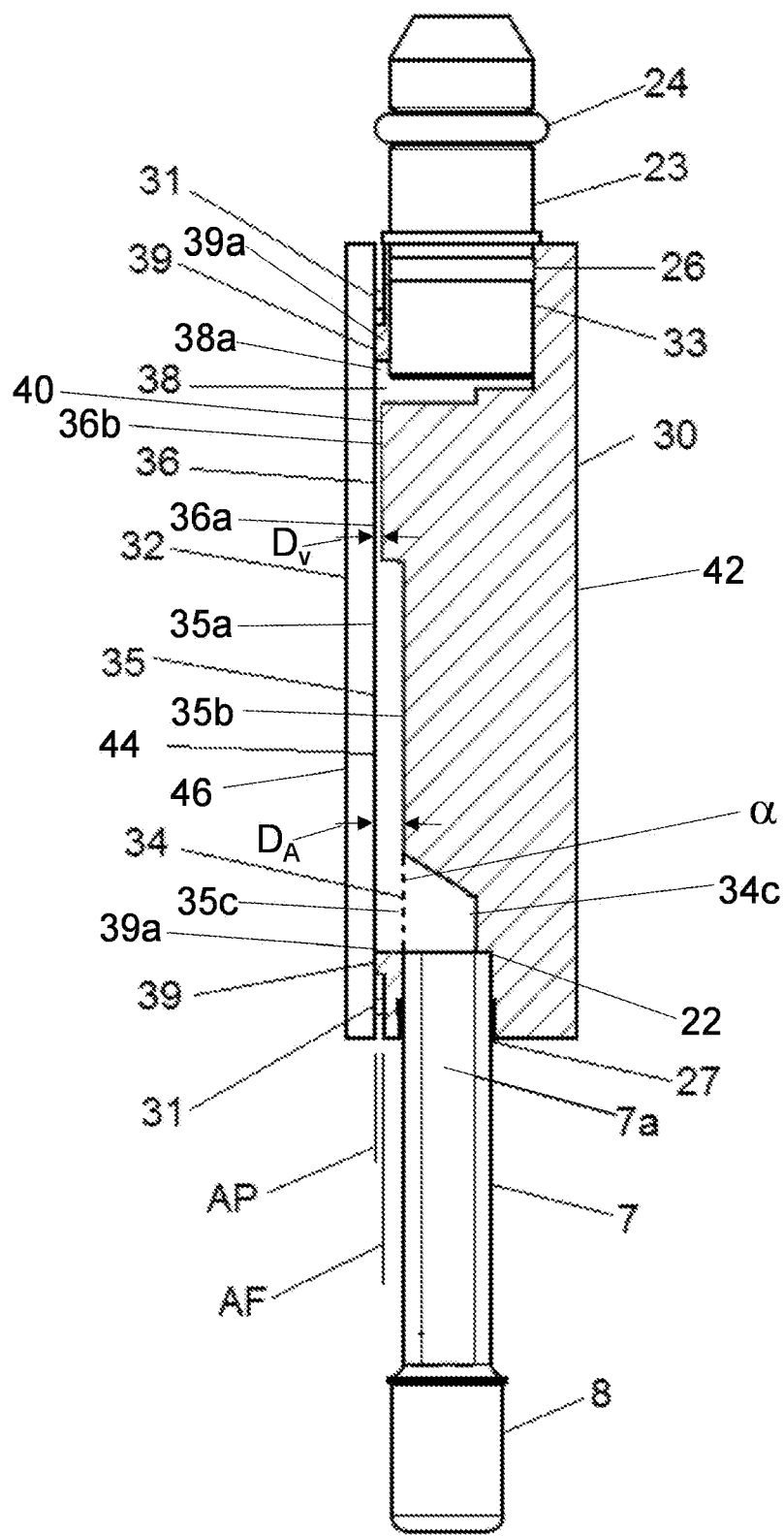
FIG. 6 is a cross-sectional side view of immersion sampling probe of FIG. 3 taken along a plane parallel to a longitudinal axis of the probe.

FIGS. 4-6 show the two-part sample chamber 3 of probe 10 in greater detail. The housing 30 of the sample chamber 3 has a first side or face 40 and an opposing second side or face 42 (see FIGS. 4A and 6). The first face 40 is an analysis face, meaning it is the geometric side of the housing 30 in which the sample is collected and which is thus configured to be positioned face down upon the stage of optical emission spectrograph during analysis. The down direction, in this case, is a direction toward the spark source of an OES system. The first face 40 extends between the immersion end and the opposing end of the housing 30. More particularly, the first face 40 extends in a first plane AF from the first end 16 toward the second end 18 of the sample chamber 3. At the second end 18 of the sample chamber 3, there is provided a gas port 33 which is preferably wholly contained within the housing 30. The gas port 33 receives the coupler 2 (as shown in FIG. 1 or 3) which, as described herein, is sealed to the housing 30 in a substantially gas tight manner by the adhesive 26 (see FIG. 3).

Referring to FIGS. 4 and 6, portions of the first face 40 are hollowed out to form different regions or zones of the sample chamber 3 for ventilation and the collection of molten metal. More particularly, the first face 40 of the housing 30 includes various depressions which collectively form the sample cavity of the sample chamber 3, as follows: a first region 34 proximate the first end 16 of the sample chamber 3 and in direct communication with the inflow conduit 7, a second region 35 overlying the first region 34, a third region 36 adjacent to the second region 35. The first face 40 also includes an additional depression in the form of a fourth region 38 proximate the second end 18 of the sample chamber 3 and in direct communication with the gas port 33. The gas port 33 (and thus the coupler 2) and the inflow conduit 7 are located in the housing 30, such that they are in direct communication and aligned with the sample cavity of the sample chamber 3. More particularly, the gas port 33 and the inflow conduit 7 preferably extend parallel to the sample cavity of the sample chamber 3, and more preferably the gas port 33 and the inflow conduit 7 extend along a common longitudinal axis X of the sample cavity of the sample chamber 3.

Referring to FIG. 6, the fourth region 38 is a connecting volume defined by an indentation or depression formed in the first face 40 of the housing 30 of the sample chamber 3. The connecting volume 38 thus has an open end 38a at the first face 40. The connecting volume 38 is in gas communication with the gas port 33. As the molten metal generally solidifies in the third region 36, as described herein, the connecting volume 38 is generally not considered to be part of the sample housing cavity for receiving molten metal.

The third region 36 is a ventilation zone which is in gas communication with the connecting volume 38. The ventilation zone 36 is defined by an indentation or depression formed in the first face 40 of the housing 30. The ventilation zone 36 thus has an open end 36a at the first face 40 and an opposing closed bottom end 36b. A center line of the ventilation zone 36 preferably aligns with the second region 35 and the gas coupler 2.

The second region 35 is an analysis zone. The analysis zone 35 is defined by an elongated indentation or depression formed in the first face 40 of the housing 30. The analysis zone 35 thus has an open end 35a at the first face 40 and an opposing partially closed bottom end 35b. More particularly, the physical boundary of the closed bottom end 35b only extends across a portion of the length of the analysis zone 35.

In one embodiment, the opposing ends (i.e., the leading end and the trailing end in terms of the immersion direction I) of the analysis zone 35 are rounded for ease of machining. However, it will be understood by those skilled in the art that the ends may be any shape.

A portion of the analysis zone 35 overlays the first region 34 of the sample chamber 3. More particularly, the leading end of the analysis zone 35 (i.e., the leading end of the analysis zone 35 proximate the immersion end 16 of the sample chamber 3) overlays and is in direct communication with the first region 34 (see FIG. 6). Thus, the portion of the analysis zone 35 which overlays the first region 34 is not physically bounded by the closed bottom end 35b. The first region 34 is a distribution zone which is in direct communication with the inflow conduit 7. More particularly, molten metal is introduced directly into the distribution zone 34 from the second end 22 of the inflow conduit 7. As such, the inlet conduit 7 is located so as to be in direct flow communication with the distribution zone 34 in a direction parallel to the longitudinal axis X.

Again, there is no physical delineation between the analysis zone 35 and the distribution zone 34. However, these are considered separate zones in terms of the prescribed dimensions for the practice of the invention. In particular, the imaginary boundary between the analysis zone 35 and the distribution zone 34, as indicated by a dashed line 35c on FIG. 6, is essentially an extension of the closed bottom end 35b, meaning the boundary 35c between the analysis zone 35 and the distribution zone 34 lies in the same as the closed bottom end 35b. The analysis zone 35 is preferred to be of a uniform depth overlying the distribution zone 34, as discussed in greater detail herein.

Collectively, the connecting volume 38, the ventilation zone 36, the analysis zone 35 and the distribution zone 34 form the hollow volume of the sample chamber 3. The ventilation zone 36, the analysis zone 35 and the distribution zone 34 collectively comprise the cavity receiving the molten metal, meaning the sample cavity in which the molten metal (and more particularly molten steel or iron) is introduced along the longitudinal axis X, collected, subsequently solidified to form a solidified metal sample S, and ultimately directly analyzed. The ventilation zone 36, the analysis zone 35 and the distribution zone 34 are contiguous regions.

Referring to FIGS. 4 and 6, the first face 40 of the housing 30 includes a raised portion 39 that encompasses the depressions of the connecting volume 38, the ventilation zone 36, the analysis zone 35 and the distribution zone 34. More particularly, the raised portion, herein referred to as the ridge 39, peripherally surrounds the collective volume of the connecting volume 38, the ventilation zone 36, the analysis zone 35 and the distribution zone 34. The upper or distal rim 39a of the ridge 39 is preferably at a height of 0.2 mm to 0.5 mm, and more preferably 0.3 mm, relative to the remainder of the first face 40 (i.e., relative to the first plane AF). Thus, the distal rim 39a of the peripheral ridge 39 lies in a second plane AP which is spaced apart from the first plane AF of the first face 40. The second plane AP is referred herein as the analysis plane. When the sample chamber 3 is filled with metal, the analyzable surface AS of the solidified metal sample AS lies in the analysis plane AP, as described herein in greater detail.

Figure 5A:
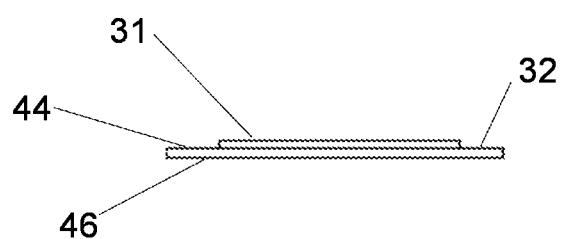
FIG. 5A is a bottom plan view of the sample chamber cover plate shown in FIG. 5.

Referring to FIGS. 5-5A, the cover plate 32 need not be formed of the same material as the housing 30. Unlike the housing 30, the cover plate 32 does not have to be formed of a material which is a good electrical conductor. For example, the cover plate 32 may be formed of fused silica or a refractory ceramic material. Preferably, however, the cover plate 32 is formed of the same material as the housing 30.

Preferably, for practical purposes of assembly, the cover plate 32 is approximately the same width and length as the housing 30. However, it will be understood that the cover plate 32 is not limited to such dimensions, and may have a width and length greater or less than that of the housing 30.

The cover plate 32 has a first side or face 44 and an opposing second side or face 46. The cover plate 32 preferably has a thickness between 1 mm and 5 mm extending from the first face 44 to the second face 46. The first face 44 of the cover plate 32 is configured to face the housing 30, and more particularly the first face 40 of the housing 30, in the assembled configuration of the sample chamber 3. A sealing member 31 is provided on the first face 44 of the cover plate 32 so as to be positioned between the housing 30 and cover plate 32 in the assembled configuration of the sample chamber 3. The sealing member 31 is preferably a gas sealing member. More particularly, the sealing member 31 is a gasket. The gasket 31 is preferably dimensioned so as to encompass or surround the ridge 39 in the assembled configuration of the sample chamber 3. The gasket 31 may be of any shape. Preferably, however, the gasket 31 is formed in the same shape as that of the ridge 39 of the first face 40 of the housing 30.

In one embodiment, the gasket 31 is formed of silicone or any similar polymer. It will be understood by those skilled in the art that the gasket 31 may be formed of any material which would provide a gas tight seal between the cover plate 32 and the housing 30. After the material of the gasket 31 is applied to the first face 44 of the cover plate 32, the gasket 31 is allowed to dry before the cover plate 32 is assembled with the housing 30 and secured together by the clamp 4, thus ensuring that the gasket 31 does not adhere to the housing 30.

It will be understood by those skilled in the art that the gasket 31 may alternatively be formed as an O-ring or of a flat gasket material without departing from the scope of the invention. For example, in another embodiment, the gasket 31 is a plastic foil applied as a flat gasket,—preferably having a thickness of 0.04 to 0.1 mm. For example, the flat gasket may be formed of the surface protection tape, Product No. 4011a, manufactured by 3M™.

In the assembled configuration of the sample chamber 3, as shown in FIG. 6, the cover plate 32 and the housing 30 are assembled together along the analysis plane AP to form the sample cavity including the distribution zone 34, the analysis zone 35 and the ventilation zone 36. More particularly, the cover plate 32 rests on the ridge 39 of the housing 30 (i.e., in the analysis plane AP) and the gasket 31 contacts the first face 40 of the housing 30 such that the gasket 31 surrounds or encompasses the ridge 39. More particularly, in the assembled configuration of the sample chamber 3, the cover plate 32 sits flush against the ridge 39 in the analysis plane AP and is sealed to the first surface 40 of the housing 30 in a gasket-type fit due to the seal of the gasket 31 against the first surface 40.

Thus, the cover plate 32 closes the sample cavity of the sample chamber 3. Again, the sample cavity of the sample chamber 3 is the volume in which molten metal is introduced along the longitudinal axis X from the inflow conduit 7, collected and subsequently rapidly cooled to form the solidified metal sample S, and more particularly solidified steel or iron strip-shaped sample S. As such, there are only two openings formed in the assembled sample chamber 3, namely the first opening 20 in communication with the inflow conduit 7 and the opening of the gas port 33 in communication with the coupler 2. No portion of the cover plate 32 contributes to the volume of the retrieved solidified metal sample. The analysis surface of the solidified steel or iron sample S housed with the sample cavity lies in the analysis plane AP. Further, the first opening 20 and the associated inflow conduit 7 and the gas port 33 and the associated coupler 2 are spaced apart from and do not intersect the analysis plane AP.

Hereinafter, a length L of each zone 34, 35, 36 is described in terms of a dimension parallel to and aligned with the longitudinal axis X of the sample cavity, a width W of each region 34, 35, 36 is described in terms of a dimension perpendicular to the longitudinal axis X; and a depth D of each zone 34, 35, 36 is described in terms of a dimension perpendicular to the longitudinal axis X and perpendicular to the width dimension. More particularly, a depth of each zone 34, 35, 36 is measured from a point along the analysis plane AP to the bottom end or boundary of each zone 34, 35, 36, because the sample cavity of the sample chamber 3 is bounded on one end by the zones 34, 35, 36 and on the other end by the cover plate 32 lying in the analysis plane.

Figure 11:
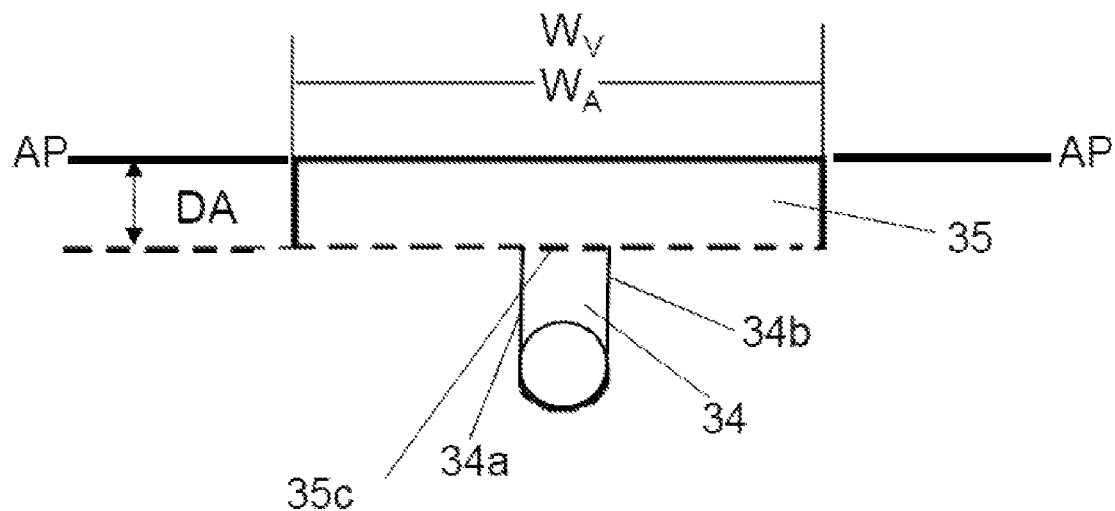
FIG. 11 is a cross-sectional view of the sample cavity of the sample chamber housing of FIG. 4 taken along a plane perpendicular to a longitudinal axis of the probe.

The length L, width W and depth D dimensions are most clearly shown in FIG. 4, FIG. 6 and FIG. 11. The cross-sectional area dimension, discussed herein, is equivalent to a width W dimension multiplied by a depth D dimension (see FIG. 11).

The analysis zone 35 has a width $W_A$ of between 8 and 12 mm, preferably 10 mm. The length $L_A$ of the analysis zone 35, extending from the leading end to the trailing end (the trailing end of the analysis zone corresponding to the leading end of the ventilation zone 36) is 25 to 35 mm, preferably 30 mm. The depth $D_A$ of the analysis zone 35 extends from a point along the analysis plane AP to the closed bottom end 35b and boundary 35c (i.e., the base of the depression). The depth $D_A$ of the analysis zone 35 is 0.5 mm to 3 mm, preferably 2 mm.

In one embodiment, the width $W_A$ of the analysis zone 35 tapers slightly along the longitudinal axis X, such that the cross-sectional area of the analysis zone 35 (i.e., the cross-sectional area of the analysis zone 35 taken along the plane perpendicular to the longitudinal axis X as shown in FIG. 11) is at a maximum proximate the immersion end 16 of the sample chamber 3 and tapers slightly toward the ventilation zone 36. More particularly, the walls defining the width $W_A$ of the analysis zone 35 (i.e., the walls extending perpendicular to the first face 40) are slightly tapered in the direction of the longitudinal axis X, such that the width $W_A$ of the analysis zone 35 is greater at the first end 16 of the sample chamber 3 proximate the inflow conduit 7 and decreases in the direction of the longitudinal axis X toward the ventilation zone 36. As such, the analysis zone 35 can accommodate shrinkage of the solidifying molten metal without undue stress on the thin cross section of the solidified metal sample S.

The cross-sectional area of the inflow conduit 7, that is the cross-section of the inflow conduit 7 taken along the plane perpendicular to the longitudinal axis X as shown in FIG. 11, is dependent upon the cross-sectional area of the analysis zone 35 and the distribution zone 34. Preferably, the cross-sectional area of the inflow conduit 7 is between 0.5 and 2 times the cross-sectional area of the analysis zone 35. More particularly, the ratio of the inflow conduit 7 to the analysis zone 35 is more than 0.5 and less than 2. Preferably, the cross-sectional area of the inflow conduit 7 is between 0.20 and 0.70 times the largest cross-sectional area of the distribution zone 34 and thus lowers the inlet velocity required for metal mixing, including for the incorporation of any deoxidants. More preferably, the cross-sectional area of the inflow conduit 7 is 0.55 times the largest cross-sectional area of the distribution zone 34. If the cross-sectional area of the inflow conduit 7 is too small (i.e., less than 0.5 times the cross-sectional area of the analysis zone 35 and/or less than 0.20 times the largest cross-sectional area of the distribution zone 34), then there is not enough deceleration of the inflowing molten metal to accomplish optimum mixing of deoxidants and reducing turbulent flow, and there is poor filling. If the cross-sectional area of the inflow conduit 7 is too large (i.e., greater than 2 times the cross-sectional area of the analysis zone 35 and/or greater than 0.70 times the largest cross-sectional area of the distribution zone 34), then the distribution zone 34, when filled, adds sensible heat to the molten metal sample that must be removed by more housing 30 mass, thus moving further from an economic solution.

The distribution zone 34, as described earlier, lies under the analysis zone 35 and therefore does not influence the overall length $L_A$ of the analysis zone 35. The volume of the distribution zone 34 is bounded by the analysis zone 35, and more particularly by the boundary 35c, on its upper end, as well as by its opposing side walls 34a, 34b and its bottom surface 34c (see FIG. 11). The side walls 34a, 34b are substantially perpendicular to the analysis plane AP. The width $W_D$ of the distribution zone 34 (i.e., the distance spanning the side walls 34a, 34b) also preferably does not exceed the width $W_A$ of the analysis zone 35 and is preferably not less than the inner diameter of the inflow conduit 7. Preferably, the width $W_D$ of the distribution zone 34 is equal to the inner diameter of the inflow conduit 7. A first portion of the bottom surface 34c (i.e., the surface opposite to the analysis zone 35) of the distribution zone 34 extends in a horizontal plane parallel to the longitudinal axis X. A second portion of the bottom surface 34c is angled, and more particularly extends upwardly at an angle α, and intersects with the closed bottom end 35b of the analysis zone 35 at an angle α between 40° and 90°, preferably 60°. The distribution zone 35 ends at this intersection. As such, the depth of the distribution zone 34 decreases in the flow direction of the molten metal from the inflow conduit 7 toward the gas coupler 2.

The depth $D_V$ of the ventilation zone 36 ranges between approximately 0.1 and 1 mm, the length $L_V$ of the ventilation zone 36 is approximately 5 mm, and the width $W_V$ of the ventilation zone 36 is preferably equal to or less than the width $W_A$ of analysis zone 35. The depth $D_V$ of the ventilation zone 36 is at its maximum at the end closer to the immersion end 16 of the sample chamber 3. That is, the depth $D_V$ of the ventilation zone 36 decreases slightly from the immersion direction I toward the connecting volume 38. More particularly, a gradual reduction in the depth $D_V$ of the ventilation zone 36 from the trailing end of the analysis zone 35 to the end of the ventilation zone 36 from 1 mm to 0.2 mm is preferred.

There are no increases in the width of the sample cavity after the end of the distribution zone to the gas coupler or increases in the depth dimensions of the sample cavity in the flow direction of the molten steel or iron from the inflow conduit 7 toward the gas coupler 2, such that the metal shrinking during solidification can freely move towards the inflow conduit 7.

The cross-sectional area of the analysis zone 35 (i.e., the width $W_A$ of the analysis zone 35 multiplied by the depth $D_A$ of the analysis zone 35) is between 2.5 and 10 times the cross-sectional area of the ventilation zone 36 (i.e., the width $W_V$ of the ventilation zone 36 multiplied by the depth $D_V$ of the ventilation zone 36). Therefore, the maximum cross-sectional area of the ventilation zone 36 is between 2 and 8 $mm^2$.

The various zones 34, 35, 36 of the sample chamber 3, as discussed above, correspond to different portions of the solidified metal sample S formed in the sample chamber 3. As such, the dimensions of the ventilation zone 36, analysis zone 35 and distribution zone 34 correspond to the dimensions of various portions of the solidified metal sample S formed therein. For example, a depth of each of the zones 34, 35, 36 corresponds a thickness of a corresponding portion of the solidified metal sample S.

Figure 8:
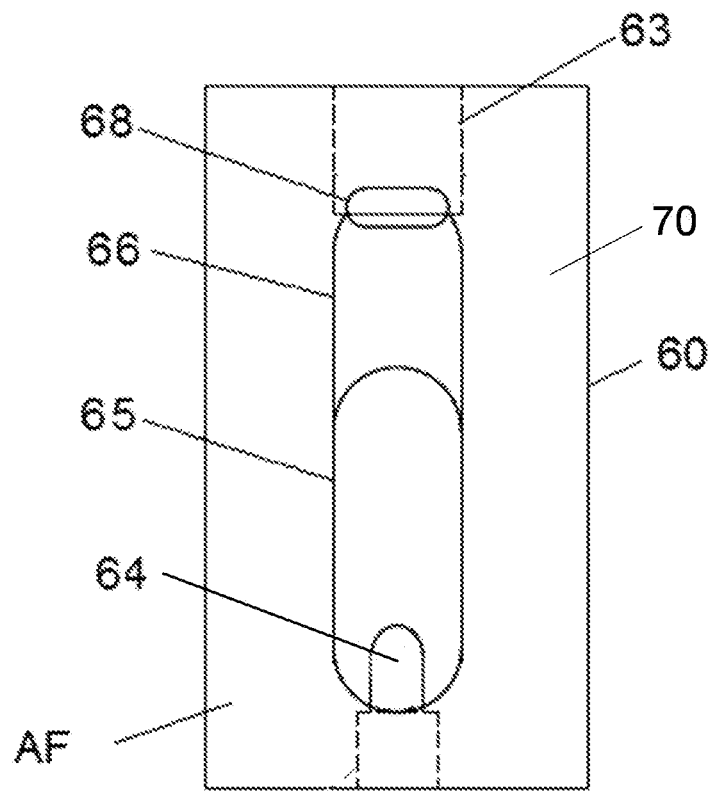
FIG. 8 is a front elevational view of the housing of a two-part sample chamber in accordance with another embodiment of the invention.
Figure 8A:
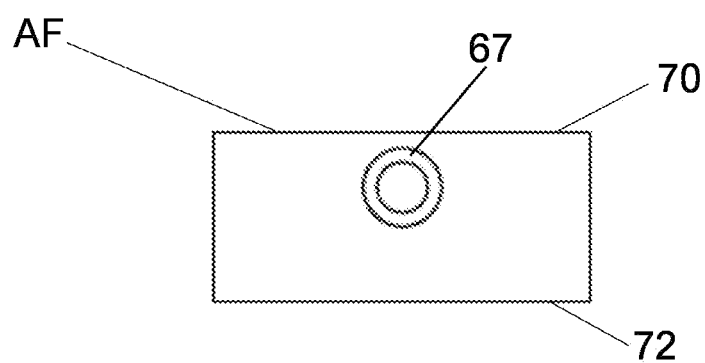
FIG. 8A is a bottom plan view of the sample chamber housing shown in FIG. 8.
Figure 9:
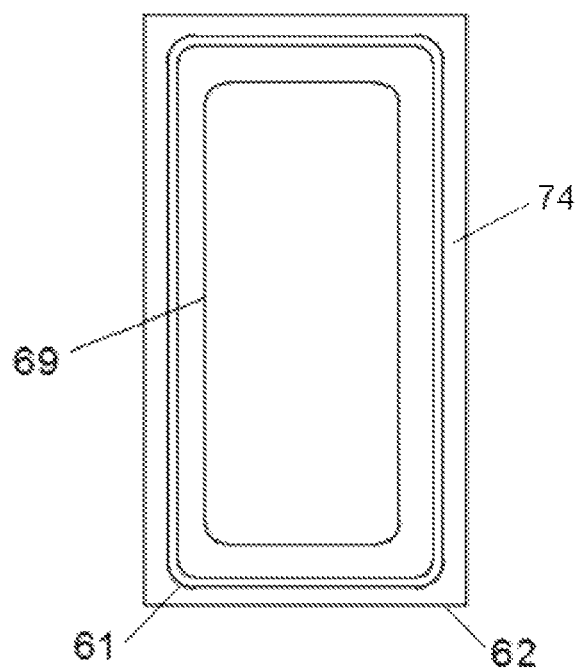
FIG. 9 is a front elevational view of the cover plate configured to be assembled with the sample chamber housing of FIGS. 8-8A.
Figure 9A:
FIG. 9A is a bottom plan view of the sample chamber cover plate shown in FIG. 9.

FIGS. 8-9A show an alternative sample chamber which is essentially the same as the sample chamber 3, except for certain differences in the configurations of the housing 60 and cover plate 62, as discussed hereinafter. The housing 60 includes an connecting volume 68, a ventilation zone 66, an analysis zone 65 and a distribution zone 64 which are the same as the connecting volume 38, a ventilation zone 36, an analysis zone 35 and a distribution zone 34, respectively, of the housing 30. The housing 60 is also provided with a gas port 63 at one end, similar to the gas port 33 of the sample chamber 3, and an inflow conduit 67, similar to the inflow conduit 7 of the sample chamber 3. The housing 60 also has a first side or face 70 which is an analysis face and which extends in a first plane AF, and an opposing second face 72. Unlike the housing 30, the housing 60 does not include a raised ridge (i.e., the raised ridge 39 of the housing 30). Referring to FIGS. 9-9A, the cover plate 62 has a first face 74 configured to face the housing 60 in the assembled configuration of the sample chamber. A gasket 61 is provided on the first face 74 of the cover plate 62 so as to be positioned between the housing 60 and cover plate 62 in the assembled configuration of the sample chamber. Unlike the cover plate 32 of the sample chamber 3, the cover plate 62 further includes a raised central portion 69 extending from its first face 74. The raised central portion 69 has a height between 0.2 mm and 0.5 mm, preferably 0.3 mm. The gasket 61 surrounds or encompasses the raised central portion 69.

In the assembled configuration of the sample chamber, the raised central portion 69 of the cover plate 62 sits flush against the housing 60, with gasket 61 to sealing to the first face 70 of the housing 60. Thus, the cover plate 62 closes the open volume of the sampling chamber hollowed out from the material of the housing 60 to form the connecting volume 68, a ventilation zone 66, an analysis zone 65 and a distribution zone 64. In this embodiment, analysis plane AP is equal to the plane AF of the analysis face 70.

Figure 10:
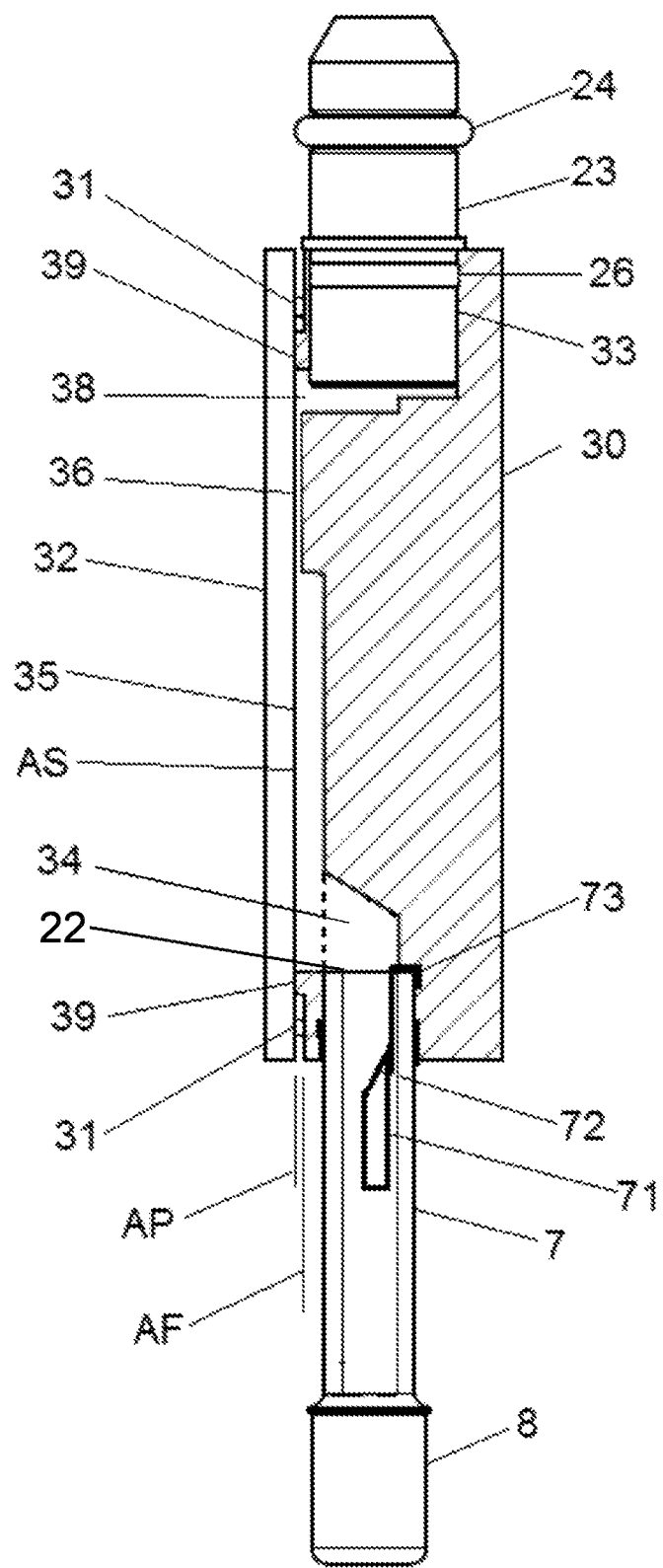
FIG. 10 is a cross-sectional side view of immersion sampling probe including a deoxidant, in accordance with another embodiment of the invention, taken along a plane parallel to a longitudinal axis of the probe.

Referring to FIG. 10, there is shown an alternative embodiment of the sample chamber 3, 3', further including a deoxidant in the form of a strip 71. Various reference numerals utilized to describe the sample chamber 3 shown in FIG. 6 are repeated on FIG. 10, but are not repeated herein regarding the discussion of FIG. 10, as they identify the same components already described with respect to FIG. 6. The deoxidant is preferably aluminum, but may alternatively be zirconium, titanium or other such deoxidants known in the art. The width and thickness of the deoxidant strip 71 are approximately 2 mm and 0.1 mm, respectively. The deoxidant strip 71 is anchored to the inflow conduit 7 at its second end 22 opposite the immersion direction I by a bend 73 over the second end 22 of the inflow conduit 7, thereby resisting the force of the purge gas to inject the metal deoxidant strip 71 into the molten bath. The length of the metal deoxidant strip 71 is preferably as long as the length of the inlet conduit 7 that is enclosed by the measuring head 5. A portion 72 of the metal deoxidant strip 71 located in the inflow conduit 7 is preferably twisted by at least 90° in order to position its width perpendicular to the wall inflow conduit 7.

Rapid chill of the molten metal collected in the sample chamber 3 is achieved largely due to the relationship between the mass of the sample chamber 3 (i.e., the mass of the cover plate 32 plus the mass of the housing 30) and the volume of the collected molten metal which is converted to a mass. In the case of molten steel, which has an approximate molten density of 7 $g/cm^3$, or in the case molten iron, which has an approximate molten density of 6.8 $g/cm^3$, the ratio of the mass of the sample chamber 3 to the mass of the molten metal collected within the sample chamber 3 (calculated based on the volume collected therein) is preferably in the range of 9 to 12, more preferably 10, in order to ensure an oxide free analysis surface AS.

Thus, while the internal voids of the analysis zone 35, ventilation zone 36 and distribution zone 34 preferably satisfy the specific dimensional criteria described above, the overall dimensions of the sample chamber 3 (composed of the cover plate 2 and the housing 30) also preferably satisfy certain criteria to achieve the desired mass ratio of the mass of the sample chamber 3 to the mass of the molten metal collected within the sample chamber 3. One skilled in the art would understand that the overall width, depth and/or length of the housing 30 or cover plate 32 may be adjusted as necessary to increase or decrease the mass of the housing 30, without changing the internal voids necessary to create the sample cavity.

In particular, once allowances are made for the outer diameters of both the second end 22 of the inflow conduit 7 and the gas coupler 2, such that both are wholly contained within the sample housing, one or more dimensions of the housing 30 can be easily adjusted to meet the mass ratio requirement in order for the mass of the sample chamber 3 (where the cover plate 32 accounts for 10 to 20% of the mass of the sample chamber 3) to be between 9 to 12 times, preferably 10 times, the mass of the metal sample S.

In order to retrieve a molten metal sample suitable for analysis using an OES from a molten metal bath according to the invention, the following examples provide exemplary procedures and configurations according to the invention, but it will be understood that many other procedures and configurations are possible within the scope of the invention. In particular, it will be understood that procedural steps such as pursuing of the sample cavity are optional steps.

Example 1

The probe 10 including the sample chamber 3 shown in FIG. 6 is pneumatically coupled to the probe holder with the simple push-on, pull off connector 23. The connector 23 is either directly attached to the sampling chamber 3 by the coupler 2 or at a distance joined by a pneumatic line. Closing of the gas circuit provides for a slight overpressure of inert purge gas. Using the probe holder for mechanical advantage, the probe 10 is immersed in a molten metal bath and remains at a predetermined distance beneath the metal surface for a specified duration. During this immersion, the protective cap 9 of the measuring head 5 which is designed to withstand destruction while passing through the slag floating upon the metal surface, melts away, thus exposing the smaller protective cap 8 of the inflow conduit 7. As the first protection cap 4 also subsequently melts, the overpressure of inert gas is released and the inert purge gas flows from the probe holder through the gas connector 23 (if present) and the coupler 2 into the connecting volume 38, the ventilation zone 36, the analysis zone 35, the distribution zone 34 which underlies the analysis zone 35, and the internal volume 7a of the inflow conduit. The gas connector 23 (if present) and the coupler 2 are adhered to the housing 30 in a substantially gas tight manner by adhesive 26 and the inflow conduit 7 is adhered to the housing 30 in a substantially gas tight manner by adhesive 27. More particularly, the second end 22 of the inflow conduit 7 is wholly contained within the housing 30 and adhered therein in a substantially gas tight manner by adhesive 27.

This purge gas removes the potentially oxidizing ambient atmosphere initially within the sampling chamber 3 and continues to flow for a few more seconds which allows for remnants of the second protective cap 9 and any slag that had been dragged down attached to the measuring head 5 to be flushed away. The pneumatic valves are then switched momentarily from purge to exhaust or vacuum, such that the direction of the purge gas is reversed to remove the overpressure, particularly by allowing the excess pressure within the sample chamber 3 to exhaust by the reverse route as mentioned above and exit the sample chamber 3. With this, molten metal from the molten metal bath (not shown) enters into and fills the inflow conduit 7 and debouches from the volume 7a of the inflow conduit 7 into the distribution zone 34 of the sample chamber 3. The molten metal is then fed to the analysis zone 35 which overlies the distribution zone 34 and fills the analysis zone 35. A portion of the molten metal will continue to flow towards the coupler 2 at the second end of the sample chamber 3, thereby at least partially or even completely filling the narrow ventilation zone 36. The probe holder now moves in the opposite direction removing the filled sample chamber from the molten bath. One skilled in the art will recognize that the basic description of the probe holder and the pneumatic valves and switches necessary to carry out pneumatically assisted sampling are known in the art and not part of the present invention.

The small size of the retrieved molten steel or iron is chilled by the housing 30 and cover plate 32, even as the measuring probe is removed from the process vessel. The rate of heat extraction from the molten sample cools the molten metal from temperatures as high as 1750° C. to 100° C. or room temperature within one minute, which essentially eliminates all external cooling required in conventional sampling and allows immediate de-molding without the potential of surface oxidation that would normally occur when exposing a hot metallic surface to an oxygen containing atmosphere.

Figures 7, 7A:
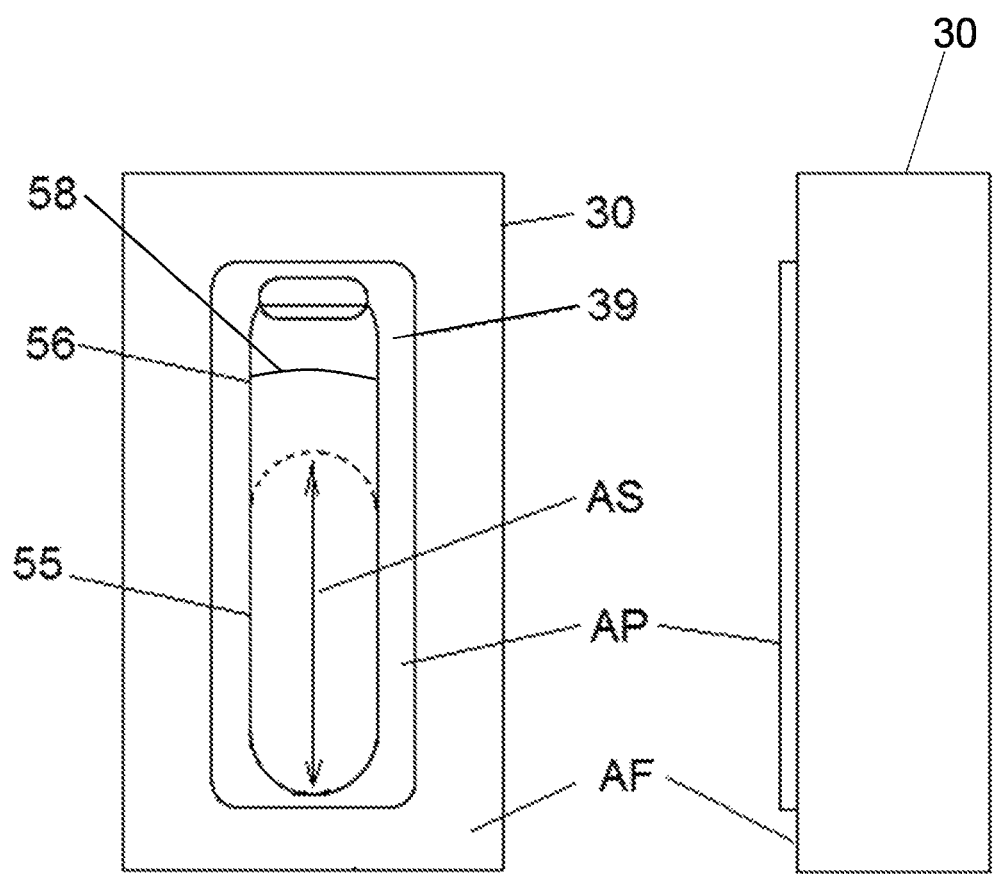
FIG. 7 is a front view of the sample chamber housing shown in FIG. 6 containing a solidified metal sample therein and suitable for OES analysis without preparation.
FIG. 7A is a side view of the sample chamber housing shown in FIG. 7.

When the molten metal freezes in the sample chamber 3, the solidified metal sample S is formed inseparably from the housing 30, as shown in FIGS. 7-7A.

The slight taper in the ventilation zone 36 promotes chilling of the molten metal before it reaches the gas coupler 2 and ensures that the solidified metal sample can shrink towards the analysis zone 35. More particularly, the molten metal which fills the ventilation zone 36 preferably freezes in the ventilation zone 36 fully before reaching the connecting volume 38.

The molten metal freezes in the analysis zone 35 against the cover plate 32, and more particularly against the first surface 44 of the cover plate 32, thereby forming the analysis surface AS of the sample S which is the surface configured to be positioned face down upon the stage of optical emission spectrograph during analysis of the sample S. The analysis surface AS extends in the plane where the first face 44 of the cover plate 32 directly contacts the surface formed by the ridge 39 (i.e., the analysis plane AP). Referring to FIGS. 7-7A, the analysis surface AS extends in the same plane as the ridge 39 of the housing 30, namely the analysis plane AP. More particularly, both the analysis surface AS of the solidified metal sample S which abuts the first surface 44 of the cover plate 32 and the metal ridge 39 in contact with the first surface 44 of the cover plate 32 extend the analysis plane AP to help close the opening of the OES.

The measuring head 5 is easily fractured allowing removal of the sampling chamber 3 from the carrier tube 1 in the forward, immersion direction I. The clip 4 holding the two part sample chamber 3 is removed. Referring to FIGS. 7-7A, there is shown the disassembled sample chamber 3. Unlike conventional sampling devices, the sample S remains attached to the sample housing 30. Therefore, the term "sample", when referring herein to the metal coupon delivered to the OES, refers to the inseparable combination of the retrieved solidified sample and the sample housing 30.

More particularly, FIGS. 7-7A show the housing 30 containing a solidified metal sample S inseparably contained therein with the cover plate 32 not shown as it has been disassembled from the housing 30. The analysis surface AS comprises the surface of the portion 55 of the sample S formed in the analysis zone 35 which sits above the metal filling distribution zone 34. The remaining portion 56 of the sample S extending from and contiguous with the analysis zone portion 55 is made up of metal which has flowed into and solidified within the ventilation zone 36. The remaining portion 56 of the sample S may thus include irregularities, such as the irregular structure 58, which do not influence the subsequent OES analysis. The analysis surface AS lies in the analysis plane AP and there are no parts or extraneous adhering materials which may break the analysis plane AP. That is, the inseparability of the sample S and the housing 30 results in an extension of the housing 30 on either side of the solidified metal, namely by the ridge 39, along the analysis plane.

The sample (i.e., the housing 30 containing the solidified metal sample S, in the form shown in FIGS. 7-7A) is then delivered to the OES by conventional means and directly analyzed by the OES without surface preparation. The rapid chill of the sample S avoids the surface oxidation normally encountered during the de-molding step. This eliminates the need for mechanical grinding and facilities rapid analysis of the sample S and reporting the chemistry to the metal process awaiting these results. Because the inflow conduit 7 and the gas port 33 (as well as the gas coupler 2) are situated within the housing 30 spaced apart from, and more particularly below, the analysis plane (as well as below the analysis face 40), rather than straddling both sides as is normally encountered in prior art clamshell molds where these components lie along the mold parting line, it is not necessary to remove the inflow conduit 7 and the gas coupler 2 from the housing 30, in order to obtain an oxide free surface, thus allowing for the creation of a solidified metal sample that can be directly placed on an OES without preparation (i.e., preparation free analysis). That is, no part of the inflow conduit 7 and gas port 33/gas coupler 2 intersects with the analysis plane AP, such that the inflow conduit 7 and the gas port 33/gas coupler 2 do not interfere with the analysis plane AP.

It was also found that filling the sample cavity along the same longitudinal axis X as the sample analysis surface AS improves the homogeneity of the sample.

Example 2

A solidified metal sample S suitable for analysis using an OES from a molten metal bath was retrieved by the same procedure as used for Example 1, except that the probe 10 included a sample chamber 3 configured as shown in FIGS. 8-9A. Thus, the resulting sample S was inseparably contained with the housing 60, with the analysis surface AS extending in the plane where the raised central portion 69 of the cover plate 62 sits flush against the first face 70 of the housing 60. As such, the mass and surface area of the housing 60 which are in contact with the cold OES instrument are maximized.

Figure 12:
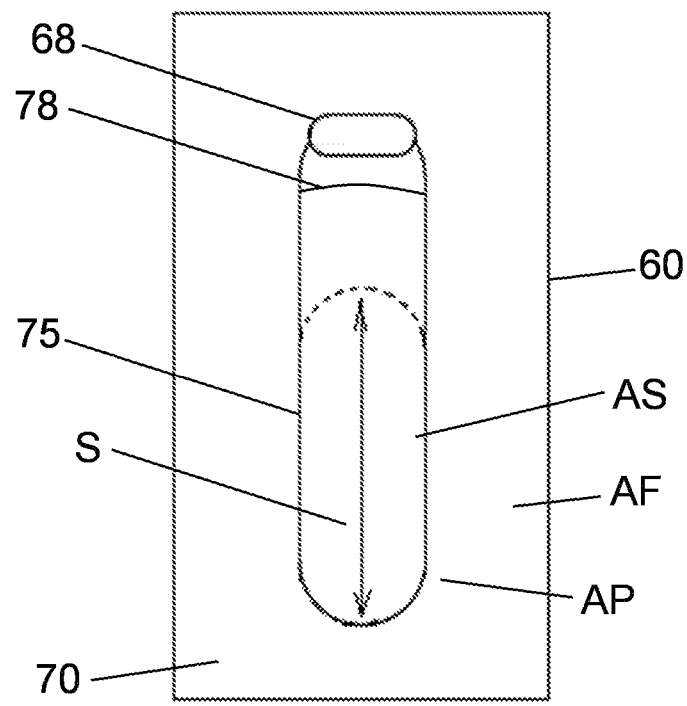
FIG. 12 is a front view of the sample chamber housing shown in FIGS. 8-8A containing a solidified metal sample therein and suitable for OES analysis without preparation.
Figure 12A:
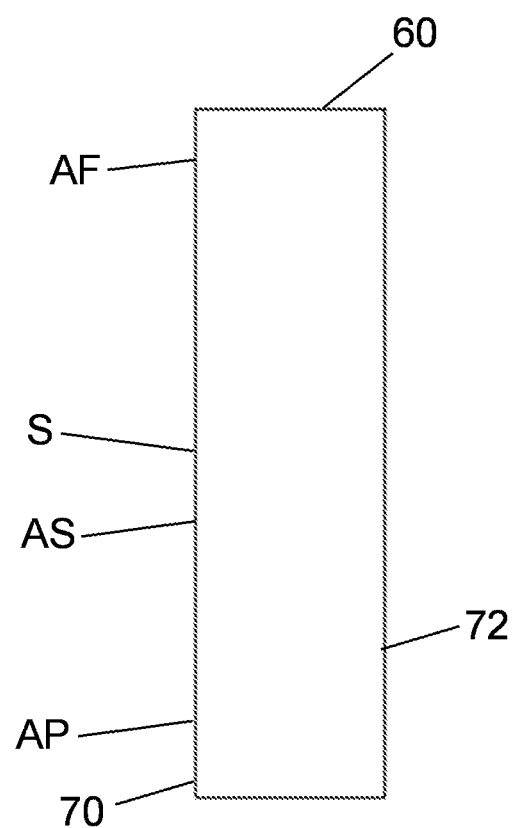
FIG. 12A is a side view of the sample chamber housing shown in FIG. 12.

More particularly, FIGS. 12-12A show the housing 60 containing a solidified metal sample S inseparably contained therein with the cover plate 62 not shown as it has been disassembled from the housing 60. The analysis surface AS comprises the surface of the portion 75 of the sample S formed in the analysis zone 65, a portion of which sits above the metal filling distribution zone 64. The remaining portion 76 of the sample S extending from and contiguous with the analysis zone portion 75 is made up of metal which has flowed into and solidified within the ventilation zone 66. The remaining portion 76 of the sample S may thus include irregularities, such as the irregular structure 78, which do not influence the subsequent OES analysis. The analysis surface AS lies in the analysis plane AP and there are no parts or extraneous adhering materials which may break the analysis plane AP. The analysis face 70 (i.e., the first face 70 of the housing 60) also lies in the analysis plane AP (i.e., plane AF is equal to the plane AP). That is, the inseparability of the sample S and the housing 60 results in an extension of the housing 60 on either side of the solidified metal, namely by the first face 70, along the analysis plane AP.

One skilled in the art can understand from the above Examples that the sample chamber 3 could be used in any known type of sampling devices and sampling application.

The advantages of the present invention are best understood in light of molten metal processes that are very fast and where overtreatment of metal and/or over processing of a heat can result in high additional expense in terms of time and materials that could have been avoided by a readily available metal chemistry at the process location.

The invention provides a solution to the shortcomings of the prior art by providing a solidified sample of metal, preferably steel or iron, fulfilling the following requirements:

- a metal sample that is analysed on an optical emission spectrometer,
- a metal sample, which at its largest cross section, has a depth of between 0.5 mm and 3 mm, preferably 2 mm,
- a solid metal sample without gas porosity and slag entrapment,
- a flat, as-retrieved analysis surface without fluid flow lines fixing the distance from the surface to the anode of the OES,
- a sample surface free of oxidation,
- a homogeneous metal sample of a maximum thickness perpendicular to the analysis plane to eliminate areas of metal and non-metallic segregation,
- a sample analytical surface spanning approximately 10 mm×30 mm and thereby providing sufficient surface area to obtain at least 2, preferably 4 sparks,
- a sample surface that lies in the same plane as the sample housing into which the sampled metal was chilled, such that the plane of the sample analytical surface is extended without interruption in both surface directions by the sample housing 30, 60 (i.e., by the ridge 39 in the sample housing 30 as shown in FIGS. 7-7A or by the first face 70 of the sample housing 60 as shown in FIGS. 12-12A) with a variation of less than 0.1 mm, and
- a sample surface which is thermally maintained during OES analysis by the attached sample housing 30, 60.

The inseparability of the sample S and the housing 30, 60 results in an extension of the housing 30, 60 on either side of the solidified metal along the analysis plane provides multiple improvements over the prior art. Conventional prior art samples, which are composed entirely of just the sampled metal and are designed to accommodate the physical requirements of the OES (i.e., completely cover the analysis opening of the OES), rather than being designed to achieve geometries that promote OES accuracy, completely cover the analysis opening of the OES. Thus, conventional prior art samples have a sample size that has more material than is needed for an acceptable metal sample. During OES, the spark should not jump to the edge material of the OES sample stage, so this opening is purposefully rather large as previously described. Inert gas is purged into the spark chamber during analysis so that leaks between the sample S to be analyzed and the spectrometer stage cannot be tolerated.

The invention utilizes the inseparability of the sample S and the housing 30, 60 to also provide a portion of the housing 30, 60 surface for covering the analysis opening. The sampler housing 30, 60 extending perpendicular to the elongation axis allows for an analysis zone to be just slightly larger than the burn area of the OES spark. Because of this extension of the analysis plane AP by the sampler housing 30, 60, the volume of the molten metal filling the analysis zone 35, 65 of the sampler housing 30, 60 can be much smaller. This reduced volume translates to reduced heat input so that together the heat of the molten metal filling the distribution zone 34, 64, analysis zone 35, 65 and ventilation zone 36, 66 is substantially less than prior art devices, and therefore can be rapidly chilled to achieve a non-segregated metal sample. Further, the retrieved sample S has an elongated shape which provide for a minimum distance to the adjacent housing 30, 60 material for distribution of the heat away from the sample S during OES analysis.

That is, a relatively smaller sample volume and a relatively larger sampler housing 30, 60 volume provides the necessary mass ratio (i.e., ratio of the mass of the sample chamber 3 to the mass of the molten metal collected within the sample chamber 3 in the range of 9 to 12, more preferably 10), thereby enhancing the capability of the attached housing 30, 60 to function as a heat sink to mitigate the thermal increase of the sample during OES and, in turn, minimizing analysis variation. Thus, the inseparable assembly of the sample housing 30, 60 and solidified sample S provides beneficial functions during sample retrieval and then during sample analysis, which have not been previously discovered or recognized.

Rapid solidification of the molten metal, and thus production of a homogeneous solidified metal sample S, is possible, and more particularly optimized, because of the relatively small sampling volume (i.e., the small sample cavity formed by the distribution zone 34, the analysis zone 35 and the ventilation zone 36) and the relatively large cooling mass of the sample chamber housing 30, 60, as well as by maintaining intimate contact between the surfaces of the solidifying molten sample S and the chill housing 30, 60 of the sample chamber 3, as the sample cools and shrinks during solidification. A benefit of increased surface contact area between the housing 30, 60 and the solidifying sample S to optimize heat exchange during cooling also promotes the maintenance of the sample temperature during subsequent analysis where the energy of the OES spark will heat the small mass of the solidified metal sample S. Such analysis may occur shortly after retrieval from the molten metal bath, or minutes, hours or days later.

Importantly, the metal sample S as obtained from the molten metal remains held within the sample housing 30, 60 for analysis, as shown in FIGS. 7-7A and 12-12A, rather than being removed therefrom. More particularly, unlike prior art samplers and samples, the present invention requires an inseparability of the sample housing 30, 60, which is the largest cooling mass, and the retrieved sample S of metal, during OES analysis. Thus, during OES analysis, the solidified sample S remains secured within the housing 30, 60, which results in an extension of the housing 30, 60 on either side of the solidified metal (i.e., by the ridge 39 or the flat face 70) along the analysis plane AP.

A combined width of the analysis zone 34, 64 and adjacent portions of the housing 30, 60 is in the range of 10 mm to 30 mm. More particularly, this combined width is the effective width $W_E$ of the area to be analyzed lying in the analysis plane AP. The effective width $W_E$ comprises the width of the solidified sample S formed in the analysis zone 35, 65 (i.e., $W_A$ which is between 8 and 12 mm, preferably 10 mm) and the width of the portions of the housing 30, 60 (e.g., the ridge 39 as shown in FIG. 7) extending on either side of the sample S along the analysis plane AP.

During OES analysis, the surface of the solidified metal sample S is subjected to a high temperature arc which excites the surface atoms of the sample S to emit radiation. The sample S is then moved so that a new spark can excite a fresh surface. Typically, the analysis will be a minimum of two sparks, occasionally three and at the most 4 without preparation between sparks. In conventional small volume metal samples, the heating of the metal sample typically elevates the temperature of the sample, which results in an increasingly deviated analysis error as the sample temperature increases from the first temperature before the first spark.

In the present invention, however, the heat gained during the analysis is removed or at least mitigated by the inseparability of the sample S from the sample housing 30, 60, thereby eliminating this error of the prior art. This is a surprising result of the present invention. More particularly, it was surprisingly found that because the sample S remains secured within the sample housing 30 during the OES analysis, the temperature variation of the small volume of solidified metal is minimized. The sample housing 30, 60 to which the solidified metal sample S remains secured provides a heat sink to absorb the thermal input from the OES during analysis.

The solidified sample S is preferably formed as an elongated strip or rectangle, such that the distance between a geometric center of the solidified metal sample S to the surrounding heat sink (i.e., the housing 30, 60) is minimal. For example, where the elongated sample S has a width of 10 mm, heat from a center portion of the sample only needs to dissipate through a 5 mm mass of the sample.

During OES analysis, a spark will add heat to the sample S and the heat is then distributed (i.e., rate of distribution is in units per second) throughout the mass of the sample S. The manner in which the heat is distributed will influence the temperature measured at the surface of the sample S for each subsequent spark. Thus, the thermal diffusivity of a material has been found to be an appropriate criterion for selecting the material of the sample housing 30, 60. Thermal diffusivity is provided in units of $m^2/s$ and is equal to the thermal conductivity (W/mK)/(density $(kg/m^3)$*specific heat (J/kgK)).

Preferably, the ratio of the thermal diffusivity of the solid sampled metal to the thermal diffusivity of the sample housing 30, 60 is between 0.1 and 0.5, and more preferably is 0.2. For the sampling of molten iron or molten steel, in particular, aluminum has proven to be a good electrical and thermally conductive material to form the heat sink sample housing 30, 60, because, despite its relatively low melting temperature, the heat transfer rate of the aluminum housing 30, 60 is much higher than the heat transfer rate of the sampled iron or steel. However, it will be understood that other metals, such as copper, may be used to form the housing 30, 60, assuming the desired thermal diffusivity (heat transfer) ratio is met. Such a housing 30, 60 formed of a good electrical and thermally conductive material has been found to reduce the error in OES analysis by transferring heat to both the interior of the attached sample housing 30, 60, as well as facilitate heat transfer to the OES equipment across face 70 along the analysis plane AP.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

What is claimed is:

1. A sample chamber assembly for molten metal, the sample chamber assembly comprising:
   a cover plate and a housing,
   characterized in that the housing includes:
   an immersion end having a first opening for a molten metal inflow conduit and an opposing end; and
   a first face extending between the immersion end and the opposing end, the first face having a depression extending from proximate the immersion end toward the opposing end, the depression being in direct flow communication with the first opening and configured to receive the molten metal from the inflow conduit,
   wherein the cover plate and the housing are configured to be assembled together along a first plane to form a sample cavity including the depression, such that an analysis surface of a solidified metal sample formed within the sample cavity lies in the first plane,
   wherein the sample cavity and the first opening are aligned along a common longitudinal axis,
   wherein the first opening is spaced apart from the first plane,
   wherein a ratio of the thermal diffusivity of the solidified metal sample to the thermal diffusivity of a material forming the housing is between 0.1 and 0.5, and
   wherein the housing is configured to be inseparable from the solidified metal sample and at least a portion of the housing is directly adjacent to the solidified metal sample and lies in the first plane.

2. The sample chamber assembly according to claim 1, characterized in that a ratio of a mass of the sample chamber to a mass of the molten metal received within the sample collection volume is 9 to 12.

3. The sample chamber assembly according to claim 1, characterized in that a depth of the depression is 0.5 mm to 3 mm.

4. The sample chamber assembly according to claim 1, characterized in that the housing further includes a ridge protruding from the first face and surrounding the depression, a combined width of the depression and adjacent portions of the ridge being in the range of 10 mm to 30 mm.

5. The sample chamber assembly according to claim 1, characterized in that there are no increases in a width dimension of the sample cavity after the distribution zone in a flow direction of the molten metal from the inflow conduit toward the opposing end.

6. The sample chamber assembly according to claim 1, characterized in that a ratio of the length to depth of the sample cavity increases in a flow direction of the molten metal from the inflow conduit toward the opposing end.

7. The sample chamber assembly according to claim 1, characterized in that a total length of the depression is between 25 and 35 mm.

8. The sample chamber assembly according to claim 1, characterized in that the depression has a uniform depth and a cross-sectional area of the depression gradually tapers in the flow direction of the molten metal from the inflow conduit toward the opposing end.

9. The sample chamber assembly according to claim 1, characterized in that the solidified metal sample is formed as an elongated strip or rectangle.

10. The sample chamber assembly according to claim 1, characterized in that the cover plate includes a sealing member configured to provide a substantially gas-tight seal between the cover plate and the housing.

11. The sample chamber assembly according to claim 1, characterized in that the cover plate is secured to the housing by a metal clamp to form the sample chamber.

12. The sample chamber assembly according to claim 1, characterized in that a cross-sectional area of the inflow conduit is between 0.5 and 2 times of a cross-sectional area of the depression.

13. The sample chamber assembly according to claim 4, characterized in that when the cover plate and the housing are assembled together, the cover plate sits flush against the ridge of the housing along the first plane.

14. The use of a sampler having the sample chamber assembly according to claim 1 for obtaining a solidified metal sample that is inseparably contained with the housing of the sample chamber assembly.

15. The sample chamber assembly according to claim 1, wherein a ratio of the thermal diffusivity of the solidified metal sample to the thermal diffusivity of a material forming the housing is 0.2.

16. The sample chamber assembly according to claim 1, characterized in that a ratio of a mass of the sample chamber to a mass of the molten metal received within the sample collection volume is 10.

17. The sample chamber assembly according to claim 1, characterized in that a total length of the depression is 30 mm.

* * * * *